US006803052B2

(12) United States Patent
Faisant et al.

(10) Patent No.: US 6,803,052 B2
(45) Date of Patent: Oct. 12, 2004

(54) USE OF BIODEGRADABLE MICROSPHERES THAT RELEASE AN ANTICANCER AGENT FOR TREATING GLIOBASTOMA

(75) Inventors: Nathalie Faisant, Montreuil sur Marne (FR); Jean-Pierre Benoit, Avrille (FR); Philippe Menei, Avrille (FR)

(73) Assignee: Laboratoires des Produits Ethiques Ethypharm, Houdan (FR)

( * ) Notice: Subject to any disclaimer, the term of this patent is extended or adjusted under 35 U.S.C. 154(b) by 80 days.

(21) Appl. No.: 09/988,011

(22) Filed: Nov. 16, 2001

(65) Prior Publication Data

US 2002/0051749 A1 May 2, 2002

Related U.S. Application Data

(63) Continuation of application No. PCT/FR00/01315, filed on May 17, 2000.
(60) Provisional application No. 60/147,495, filed on Aug. 9, 1999.

(30) Foreign Application Priority Data

May 17, 1999 (FR) ............................................ 99 06207

(51) Int. Cl.⁷ ............................... A61F 2/02; A61K 9/50
(52) U.S. Cl. ......................... 424/426; 424/501; 424/502
(58) Field of Search ................................. 424/426, 501, 424/502

(56) References Cited

U.S. PATENT DOCUMENTS 5,846,565 A * 12/1998 Brem et al. .................. 424/486

FOREIGN PATENT DOCUMENTS

FR 2 693 905 1/1994

OTHER PUBLICATIONS

R. Jalil et al., "Biodegradable poly(lactic acid) and Poly-(lactide–co–glycolide) microscapsules: problems associated with preparative techniques and release properties," *J. Microencapsulation* 1990, 7(3):297–325, Taylor & Francis Ltd.
D.G. Kotsilimbas et al., "Evaluation of parenteral 5–FU on experimental brain tumores," *Neurology* 1966 16:916–918.
J.H. Kou et al., "Bioerosion and biocompatibility of poly( d,l–lactic–co–glycolic acid) implants in brain" *Journal of Controlled Release* 1997 43:123–130 Elsevier Science Ireland Ltd.
J.A. Koutcher et al., "Radiation Enhancement By Biochemical Modulation and 5–Fluorouracil," *Int. J. Radiation Oncology Biol. Phys.*, 1997 39(5):1145–1152, Elsevier Science Inc.
Robert Langer, "Polymer implants for drug delivery in the brain," *Journal fo Controlled Release* 1991, 16:53–60, Elsevier Science Publishers B.V.

V.A.Levin et al., "5–Fluorouracil and 1–(2–Chloroethyl)–3–cyclohexyl–1–nitrosourea (CCNU) Followed by Hydroxyurea, Misonidazole, and Irradiation for Brain Stem Gliomas: A Pilot Study of the Brain Tumor Research Center and the Childrens Cancer Gorup," *Neurosurgery* 14(6):679–681, Congress of Neurological Surgeons.
P. Menei et al., "Biodegradatioon and brain tissue reaction to poly(D,L–lactide–co–glycolide) microspheres," *Biomaterials* 1993 14(6):470–478, Butterworth–Heinemann Ltd.
P. Menei et al., "Fate and biocompatibility of three types of microspheres implanted into the brain," *Journal of Biomedical Materials Research* 1994 23:1079–1085, John Wiley & Sons, Inc.
D.H. Moore et al., "Case Report: 5–Fluorouracil Neurotoxicity," *Genecologic Oncology* 1990 36:152–154, Academic Press, Inc.
T.Painbeni et al., "Internal morphology of poly(D,L–lactide–co–glycolide) BCNU–loaded microspheres. Influence on drug stability," *European Journal of Pharmaceutics and Biopharmaceutics* 1998, 45:31–39, Elsevier Science B.V.
R.D. Penn et al., "Chronic Intratumoral Chemotherapy of a Rat Tumor with Cisplatin and Fluorouracil," *Appl. Neurophysiol.* 1983 46:240–244, S. Karger A.G. Basel.
Y. Oda et al., "Trial of Anticancer Pellet in Malignant Brain Tumours; 5 FU and Urokinase Embedded in Silastic," *Acta Neurochirurgica*, Suppl. 1979 28:489–490, Springer–Verlag.
W.R. Shapiro, "Studies on the Chemotherapy of Experimental Brain Tumors: Evaluation of 1–(2–Chloro–ethyl)–3–Cyclohexyl–1–Nitrosourea, Vincristine, and 5–Fluorourecil," *Journal of the National Cancer Institute* 1971 46(2):359–368.
W.R. Shapiro et al., "A randomized comparison of intra–arterial versus intravenous BCNU, with or without intravenous 5–fluorouracil, for newly diagnosed patients with malignant glioma," *J. Neurosurg.* 1992 76:772–781.
A.H. Soloway et al., "Chemotherapy of Brain Tumors. I. Transplanted Murine Ependymoblastomas," *Cancer Chemotherapy Reports*, Mar. 1964 36:1–4.

(List continued on next page.)

*Primary Examiner*—Carlos A. Azpuru
(74) *Attorney, Agent, or Firm*—Foley and Lardner

(57) ABSTRACT

The invention relates to the use of biodegradable microspheres that release a radiosensitizing anticancer agent for producing a medicament to be used simultaneously with, separately from or spread over time with a radiotherapy, for treating glioblastoma. The use of said biodegradable microspheres according to the invention results in a patient survival time of least 90 weeks, a thereapeutically effective concentration being maintained in the parenchymatous area throughout this time. The microspheres used prefereably contain 5-fluorouracile of the tumor, by intratissular injection. The radiothereapy targeting the tumorous mass is dosed at 60 Gy over approximately 6 weeks. The invention also relates to a method for producing the biodegradable microspheres by emulsion-extraction, and to a suspension containing the biodegradable microspheres obtained using this method.

26 Claims, No Drawings-

OTHER PUBLICATIONS

Y. Oda et al., "Trial of Anticancer Pellet in Malignant Brain Tumours; 5 FU and Urokinase Embedded in Silastic," *Acta Neurochirurgica*, Suppl. 1979 28:489–490, Springer–Verlag.

R.J. Tamargo et al., "Drug Delivery to the Central Nervous System: A Review," *Neurosurgery Quarterly* 1992 2(4):259–279, Raven Press, Ltd., New York.

A.I. Torres et al., "Formulation of BCNU–loaded microspheres: influence of drug stability and solubility on the design of the microencapsulation procedure," *J. Microencapsulation* 1996 13(1):41–51, Taylor & Francis Ltd.

T. Vietti et al., "Combined Effect of X Radiation and 5–Fluorouracil on Survival of Transplanted Leukemic Cells," *Journal of the National Cancer Institute*, Oct. 1971 47(4):865–870.

G.E. Visscher et al., "Biodegradation of and tissue reaction to 50:50 poly(DL–lactide–co–glycolide) microcapsules," *Journal of Biomedical Materials Research* 1985, 19:349–365, John Wiley & Sons, Ltd.

W. Shapiro et al., "A randomized comparison of intra–arterial versus intravenous BCNU, with or without intravenous 5–fluorouracil, for newly diagnosed patients with malignant glioma," *J. Neurosurg.*, 76:772–781, 1992.

P. Kornblith et al., "Chemotherapy for malignant gliomas," *J. Neurosurg.*, 68:1–17, 1988.

Benoit, J.P. et al., "Radiosensitization of Glioblastoma After Intracranial Implantation of Biodegradable 5–Fu–Loaded Microspheres: Phase I Clincial Trial," *Proceedings 1997 of the 24th International Symposium on Controlled Release of Bioactive Materials* (1997), pp. 995–996, Controlled Release Society, Inc.

Painbeni, T. et al., "Internal morphology of poly(D,L–lactide–co–glycolide) BCNU–loaded microspheres. Influence on drug stability," *European Journal of Pharmaceutics and Biopharmaceutics* (1998), vol. 45, No. 1, pp. 31–39.

N. Aoki, "Reversible Leukoencephalopathy Caused by 5–Fluorouracil Derivatives, Presenting as Akinetic Mutism," *Surg. Neurol.* 1986 25:279–282 Elsevier Science Publishing Co., Inc.

M.A. Bagshaw, "Possible Role of Potentiators in Radiation Therapy," *Symposium on Interrelationships of Recent Advances in Radiobiology and Radiotion Therapy* May 1961, 85(5):822–833.

M. Boisdron–Celle et al., "Preparation and Characterization of 5–Flurouracil–loaded Microparticles as Biodegradable Anticancer Drug Carriers," *J. Pharm. Pharmacol.* 1995m 47:108–114.

R.S. Bourke et al., "Kinetics of Entry and Distribution of 5–Fluorouracil in Cerebrospinal Fluid and Brain following Intravenous Injection in a Primate," *Cancer Research* Jul. 1973, 33:1735–1746.

H. Brem et al., "Interstitial chemotherapy with drug polymer implants for the treatment of recurrent gliomas," *J. Neurosurg.* Mar. 1991 74:441–446.

H. Brem et al., "Polymers to treat brain tumours," *Biomaterials* Nov. 1990, 11:699–701, Butterworth–Heinemann Ltd.

H. Brem, et al., "Polymers as Controlled Drug Delivery Devices for the Treatment of Malignant Brain Tumors," *Eur. J. Pharm. Biopharm.* 1993 39(1):2–7, Wissenschaftliche Verlagsellschaft mbH, Stuttgart, Fed. Rep. of Germany.

H. Brem et al., "Placebo–controlled trial of safety and efficacy of intraoperative controlled delivery by biodegradable polymers of chemotherapy for recurrent gliomas," *The Lancet*, Apr. 1995, 345:1008–1012.

D.F. Emerich et al., "Injectable Chemotherapeutic Micropheres and Glioma II: Enhanced Survival Following Implantation into Deep Inoperable Turmors," *Phamaceutical Research* 2000 17(7)776–781, Plenum Publishing Corporation.

E.J. Frazza et al., "A New Absorbable Suture," *J. Biomed. Mater. Res. Symposium* 1971 1:43–58, John Wiley & Sons, Inc.

M.A. Gerosa et al., "Improved treatment of a brain–tumor model," *J. Neurosurg* Mar. 1983 58:368–373.

T.E. Goffman et al., "Long–Term Follow–Up on National Cancer Institute Phase I/II Study of Glioblastoma Multiforme Treated with Iododeoxyuridine and Hyperfractionated Irradiation," *Journal of Clinical Oncology* Feb. 1992, 10(2):264–268.

* cited by examiner

USE OF BIODEGRADABLE MICROSPHERES THAT RELEASE AN ANTICANCER AGENT FOR TREATING GLIOBASTOMA

This application is a continuation of PCT International Application No. PCT/FR00/01315 filed May 17, 2000, which claims the benefit of Provisional Application No. 60/147,495 filed Aug. 9, 1999, and priority to French Application No. 99 06207 filed May 17, 1999.

The present invention relates to the use of biodegradable microspheres which release an anticancer agent, for treating glioblastoma.

Glioblastoma belongs to the group of rare diseases listed by the National Organization for Rare Disorders.

Malignant glial tumors are primary tumors of the central nervous system which represent, depending on the series, 13 to 22% of intracranial tumors. From a histological point of view, two types of malignant glial tumor are, in fact, distinguished, anaplastic astrocytomas and glioblastomas, the latter representing the most undifferentiated form of theses tumors.

There is currently no effective treatment against malignant glial tumors. The survival time of patients suffering from glioblastoma does not exceed one year, even if chemotherapy and radiotherapy are combined with surgery.

The treatment of malignant glial tumors is mainly limited by three phenomena.

The first is the existence of a blood-brain barrier (BBB) which isolates the central nervous system from the rest of the body. This BBB allows only liposoluble molecules which are small in size to pass. Other molecules must be administered at very high doses in order to reach the central nervous system, this being at the cost of considerable systemic side effects.

The second factor which limits the effectiveness of treatment for glial tumors is the infiltrating nature of these tumors. Since the brain is a highly functional organ, it is impossible to perform on it surgery which is exclusive in the carcinological sense of the word. The most complete exeresis possible will only be a macroscopically complete exeresis, leaving a large number of tumor cells infiltrated into the walls of the exeresis cavity. Many authors have, moreover, shown that 90% of malignant glial tumors which are operated on and treated with radiotherapy recur within a distance of two centimeters from the initial tumor site.

The last factor which limits the effectiveness of treatment for glial tumors is the low therapeutic index. Tumor cells shelter as it were behind normal tissue which is extremely fragile and sensitive to attacks, caused for example by radiotherapy or by certain anticancer agents. It is thus difficult to destroy the tumor cells without destroying the normal nerve cells.

The progress achieved in the treatment of glial tumors is insufficient (Kornblith P L, Walker M, Chemotherapy for malignant gliomas. J. Neurosurg, 68: 1–17, 1988; Shapiro W R, Green S B, Burger P C, Selker R G, VanGilder J C, Robertson J T, Mahaley S M, A randomized comparison of intra-arterial versus intravenous BCNU with or without intravenous 5-fluorouracil, for newly diagnosed patients with malignant glioma, J. Neurosurg. 76: 772–781, 1992).

Currently, conventional treatment for glioblastomas, subsequent to surgical resection, is based on external radiotherapy. It does not make it possible to achieve a survival time of more than one year. Combining radiotherapy with chemotherapy using 1-(2-chloroethyl)-3-cyclohexyl-1-nitrosourea (BCNU) is effective only on anaplastic astrocytomas. This contributes only modestly since it only increases the percentage of survivors at eighteen months, without modifying the survival time.

Furthermore, immunotherapy has never established itself in this area and gene therapy has yet to prove itself.

Experiments have been carried out on several techniques aimed at increasing the local concentration of anticancer agents, such as osmotic rupture of the blood-brain barrier, injection into the cerebrospinal fluid, intracarotid infusion and intratumor administration using subcutaneous reservoirs (Tamargo R J and Brem H, Drug delivery to the central nervous system, Neurosurgery Quarterly, 2: 259–279, 1992). None of these techniques has been able to increase the survival time of the patients and some have proved to be highly toxic.

Over the past few years, research in galenic pharmacy has allowed the development of implantable polymer systems which protect active substances against degradation and which allow their controlled local release over a given period of time while at the same time decreasing the systemic side effects. The advantages of these implantable polymer systems have recently prompted several teams to study their use in central nervous system pathologies (Langer R, Polymer implants for drug delivery in the brain, J. Controlled Release, 16: 53–60, 1991). In particular, such systems implanted into the tumor resection wall of malignant gliomas slow down tumor recurrence and prolong patient survival. Isolated malignant cells persist around the cavity left after the operation, which are responsible for 90% of recurrences, which occur within a distance of two centimeters from the operating locus. Within this area, the nervous tissue is functional and the blood-brain barrier is still intact, which limits the action of conventional chemotherapy and radiotherapy.

Diverse implantable polymer systems which release active molecules have been developed and tested in animals.

A system of biodegradable wafers which are composed of PCPP-SA (poly[1,3-bis(carboxyphenoxy)propane-co-sebacic acid]) and which release BCNU (GLIADEL®) has been developed despite modest results in clinical studies (Brem H, Polymers to treat brain tumors, Biomaterials 11: 699–701, 1990; Brem H, Mahaley M S, Vick N A, Black K L, Schold S C, Eller T W, Cozzens J W, Kenealy J N, Interstitial chemotherapy with drug polymer implants for the treatment of recurrent gliomas, J. Neurosurg 74: 441–446, 1991; Brem H, Walter K A, Langer R, Polymers as controlled drug delivery devices for the treatment of malignant brain tumors, Eur J Pharm Biopharm, 39 (1): 2–7, 1993; Brem H, Piantadosi S, Burger P C, Walker M, et al., Placebo-controlled trial of safety and efficacy of intraoperative controlled delivery by biodegradable polymers of chemotherapy for recurrent glioma, Lancet, 345: 1008–1012, 1995).

Microspheres which release BCNU have been developed but the results of studies in animals were relatively unencouraging (Torres Al, Boisdron-Celle M, Benoit J P, Formulation of BCNU-loaded microspheres: influence of drug stability and solubility on the design of the microencapsulation procedure, J. Microencapsulation, 13: 41–51, 1996; Painbéni T, Venier-Julienne M C, Benoit J P, Internal morphology of poly(D,L-lactide-co-glycolide) BNCU-loaded microspheres. Influence on drug stability, Eur. J. Pharm. Biopharm, 1998, 45, 31–39).

The subject of the present invention is the use of implantable biodegradable microspheres which release an anticancer agent, for treating glioblastoma. The use of these microspheres is combined with radiotherapy and with surgery. After exeresis of the tumor, the biodegradable microspheres which release an anticancer agent are implanted into the operating locus by intratissular injection. Radiotherapy is then carried out, within a maximum of seven days after the intervention.

By virtue of using these microspheres, the Applicant has succeeded, entirely advantageously, in doubling the survival time of patients suffering from a glioblastoma. Specifically, the use of the microspheres according to the invention makes it possible to achieve a survival time of at least 90 weeks.

Consequently, the present invention relates to the use of biodegradable microspheres which release a radiosensitizing anticancer agent, for manufacturing a medicinal product intended to be used simultaneously, separately or spread out over time with radiotherapy, for treating glioblastoma, said microspheres being intended to be implanted into the operating locus after exeresis of the glial tumor, characterized in that the microspheres containing the anticancer agent are coated with a polymer which delays the release of the anticancer agent and maintains, over time, a therapeutically effective concentration in the parenchymal space with a view to achieving a survival time for the patient thus treated at least equal to approximately 90 weeks, preferably approximately 130 weeks, even more preferably 160 weeks.

The microspheres used in the context of the invention contain an anticancer agent which is preferably hydrophilic and/or does not cross the blood-brain barrier. Advantageously, the anticancer agent does not show central neurotoxicity. This anticancer agent acts preferentially on dividing cells.

The anticancer agent consists of a radiosensitizing anticancer compound or of a mixture of anticancer compounds containing at least one radiosensitizing anticancer compound, said anticancer compound(s) being, for example, chosen from 5-fluorouracil (5-FU), platins, such as carboplatin and cisplatin, taxanes, such as docetaxel and paclitaxel, gemcitabine, VP16, mitomycin, idoxuridine, topoisomerase 1 inhibitors, such as irinotecan, topotecan and camptothecins, nitrosoureas, such as BCNU, ACNU or MCNU, methotrexate, bleomycin, adriamycin, cytoxan and vincristine, immunomodulating cytokines, such as IL2, IL6, IL12 and IL13, and inteferons.

The anticancer agent is preferably 5-FU.

5-FU is a long-standing and well known antimitotic agent. It is a hydrophilic molecule which crosses the blood-brain barrier very poorly and its activity is therefore increased by local administration (Bourke R S, West C R, Chheda G et al., Kinetics of entry and distribution of 5-fluorouracil in CSF and brain following intravenous injection in primate, Cancer Res, 33: 1735–1746, 1973; Gerosa M A, Dougherty D V, Wilson C B, Rosenblum M L, Improved treatment of a brain tumor model, Part 2: Sequential therapy with BCNU and 5-fluorouracil, J. Neurosurg. 58: 368, 1983; Kotsilimbas D G, Karpf R, Meredith S, Scheinberg L C, Evaluation of parenteral 5-FU on experimental brain tumors, Neurology, 16: 916–918, 1966; Levin V A, Edwards M S, Wara W M, Allen J, Ortega J, Vestnys P, 5-fluorouracil and 1-(2-chloroethyl)-3-cyclohexyl-1-nitrosourea (CCNU) followed by hydroxyurea, misonidazole and irradiation for brain stem gliomas: a pilot study of the brain tumor research center and the children cancer group, Neurosurgery, 14: 679–681, 1984; Oda Y, Tokuriki Y, Tsuda E, Handa H, Kieler J, Trial of anticancer pellet in malignant brain tumours, 5-FU and urokinase embedded in silastic. Proceeding of the 6th European Congress of Neurosurgery, Acta neurochirurgica, Suppl. 28: 489–490, 1979; Penn R D, Kroin J S, Harris J E, Chiu K M, Braun D P, Chronic intratumoral chemotherapy of a rat tumor with cisplatin and fluorouracil, Appl. Neurophysio, 46: 240–244, 1983; Shapiro W R, Studies on the chemotherapy of experimental brain tumors: Evaluation of 1-(2-chloroethyl)-3-cyclohexyl-1-nitrosourea, vincristine and 5-fluorouracil, J. Nat. Cancer Institute, 46(2), 359–368, 1971; Shapiro W R, Green S B, Burger P C, Selker R G, VanGilder J C, Robertson J T, Mahaley S M, A randomized comparison of intra-arterial versus intravenous BCNU with or without intravenous 5-fluorouracil, for newly diagnosed patients with malignant glioma, J. Neurosurg, 76: 772–781, 1992; Soloway A H, Mark V H, Dukat E G et al., Chemotherapy of brain tumors. I-Transplanted murine ependymoblastomas, Cancer Chemother Rep., 36: 1–4, 1964).

The activity of 5-FU is thus increased by sustained administration. 5-FU is an agent which acts by interfering with nucleic acid synthesis. Studies have shown that only 30 to 50% of the cells of a murine malignant glioma (L9), and 14 to 44% of the cells of a human malignant glioma, are dividing at any given moment. In addition, the durations of the glioblastoma cell cycle are long (20 hours for the L9 glioma, from 3 to 7 days for human glioblastoma). Now, 5-FU clearance in the plasma is rapid (30 min half-life) (Neuwelt E A, Barnett P A, Frenkel E P, Chemotherapeutic agent permeability to normal brain and delivery to avian sarcoma virus-induced brain tumors in the rodent: observation on problems of drug delivery, Neurosurgery, 14: 154–160, 1984). 5-FU cannot therefore destroy, via systemic administration or local injection, a large number of malignant cells.

5-FU is essentially active on tissues which undergo rapid renewal and is exceptionally neurotoxic. 5-FU intervenes in the synthesis of nucleic acids, which tissues with rapid growth particularly need in order to ensure their proliferation and regeneration. This is, of course, not the case of cerebral tissue, where mitoses are rare in the normal state and occur only among the glial population. The toxic effects of 5-FU which limit its administration via the general route are essentially hematological and gastrointestinal. While rare neurological side effects of 5-FU have been published, their etiopathogeny, which is relatively unknown, is probably multifactorial (blockage of the Krebs cycle by a 5-FU catabolite or exacerbation of a preexisting thiamine deficiency) (Aoki N, Reversible leukoencephalopathy caused by 5-fluorouracil derivatives, presenting as akinetic mutism, Surg Neurol, 25: 279–282, 1986; Moore D H, Fowler W C, Crumpler L S, 5-fluorouracil neurotoxicity, case report, Gynecol Oncology, 36: 152–154, 1990).

Finally, 5-FU is radiosensitizing (Koutcher J A, Alfieri A A, Thaler H et al., Radiation enhancement by biochemical modulation and 5-FU, Int. J. Radit, Biol. Phys., 39: 1145–1152, 1997). The superiority of the combination 5-FU/ radiotherapy in each of these isolated treatments was demonstrated as early as the 1960s on animal models and on tumor cells in vitro (Bagshaw M, A possible role of potentiation in radiation therapy, Amer J. Roentgenol, 85: 822–833, 1961; Vietti T, Eggerding F, Valeriote F, Combined effect of X-radiation and 5-fluorouracil on survival of transplanted leukemic cells, J. Natl. Inst., 47: 865–870, 1971). This synergy is thought to be due to synchronization of the tumor cell population and to a decrease in mechanisms of cellular repair through the 5-FU. The combination of radiotherapy and antipyrimidine (5-FU or BrudR) has already been attempted in humans (Goffman T E, Dachowski L J, Bobo H et al., Long term follow-up on national cancer institute phase I/II study of glioblastoma multiforme treated with iododeoxyuridine and hyperfractionated irradiation, J. Clinical Oncology, 10: 264–268, 1992).

The absence of clear-cut effectiveness may once again be explained by the systemic route of administration of the drugs.

When the anticancer agent is 5-FU, the concentration of anticancer agent in the cerebrospinal fluid, which mirrors the concentration in the parenchymal space, is between 3 and 20 ng/ml.

In order to limit the neurotoxicity of the anticancer agent contained in the microspheres used in the context of the invention, a neuroprotective compound may advantageously be added to said anticancer agent. This neuroprotective compound is, for example, chosen from peptide growth factors, such as NGF or BDNF.

The biodegradable microspheres used in the context of the invention are coated with a polymer which delays the release of the anticancer agent and maintains, in the parenchymal space, a therapeutically effective concentration for a period of time of at least three weeks, preferably of at least four weeks.

The polymer is chosen from ethylcellulose, polystyrene, poly(ε-caprolactone), poly(d,l-lactic acid) and poly(d,l-lactic acid-co-glycolic acid).

The polymer is preferably poly(d,l-lactic acid-coglycolic acid), or PLAGA, which is a biodegradable polymer permitted in the formulation of sustained-release galenic preparations (unlike PCPP-SA, which is not approved for large-scale clinical use).

The poly(d,l-lactic acid-co-glycolic acid) is preferably 50:50 PLAGA (i.e. containing an equal amount of lactic acid and of glycolic acid), for example Resomer® RG 506 supplied by BI Chimie, France, which has a weight-average molecular mass equal to 72 000, a polydispersity index equal to 1.8 and an inherent viscosity of 0.80 dl/g (0.1% solution of polymer in chloroform at 25° C.).

PLAGA is a hydrophobic copolymer, the degradation of which, caused by a hydrolysis reaction, gives rise to two normal biological substrates, lactic acid and glycolic acid, which are metabolized at the end of aerobic glycolysis to $CO_2$ and $H_2O$. Studies, which are already long-established, have shown that the respiratory pathway is the main pathway of elimination of these two substrates. The rate of biodegradation of PLAGA depends on the respective proportions of lactic acid and glycolic acid. PLAGA is completely biocompatible and causes a moderate foreign body reaction (Visscher G E, R L Robinson, H V Mauding, Fong J W, Pearson J E, Argentieri G J, Biodegradation of and tissue reaction to 50:50 poly(DL-lactide-co-glycolide) microcapsules, J. Biomed. Mat. Res. 19: 345–365, 1985). PLAGA is a constituent element of surgical sutures (Frazza E J, Schmidt E E, A new absorbable suture, J. Biomed. Mater. Res., 5: 43–58, 1971) and of subcutaneously implantable galenic forms (Jalil R, Nixon J R, Biodegradable poly(lactic acid) and poly(lactide-co-glycolide) microcapsules: problems associated with preparative techniques and release properties (Review), J. Microencapsulation, 7: 297–325, 1990). It has been demonstrated that 50:50 PLAGA microspheres may be sterilized by γ-irradiation, and that, once implanted by stereotaxy into the brain of a rodent, they are completely biodegraded within two months, causing only moderate reaction of the nonspecific astrocyte and histiocyte type (Menei P, Daniel V, Montero-Menei C, Brouillard M, Pouplard-Barthelaix A, Benoit J P: Biodegradation and brain tissue reaction to poly(DL-lactide-co-glycolide) microspheres, Biomaterials 14: 470–478, 1993; Menei P, Croue A, Daniel V, Pouplard-Barthelaix A, Benoit J P: Fate and biocompatibility of three types of microspheres implanted into the brain, J. Biomed Mat Res, 28, 1079–1085, 1994). The latter result has since been confirmed by Kou J H, Emmett C, Shen P et al., Bioerosion and biocompatibility of poly(d,1-lactic-co-glycolic acid) implants in brain, J Control Release, 43, 123–130, 1997.

The biodegradable microspheres of the invention preferably have a mean diameter of 48±20 μm, preferably 46±7 μm. They contain 15 to 35% by weight of anticancer agent, preferably from 19 to 27% of 5-FU, even more preferably 20% of 5-FU, and 65 to 85% by weight of polymer.

In the context of the present invention, the 50:50 PLAGA microspheres vehiculing 5-FU are particularly preferred.

In vitro, the 50:50 PLAGA microspheres vehiculing 5-FU can release 5-FU for 21 days. In vivo, implanted subcutaneously in rabbits, these microspheres make it possible to obtain a plateau concentration of 5-FU in the plasma for 23 days. Still in vivo and in the rodent brain, the crystals of 5-FU are visible in the microspheres at least up to the 19th day. In rabbits, after intracerebral implantation of PLAGA-5-FU microspheres, (7 mg/kg of 5-FU), no trace of 5-FU is detected in the serum, which leads to the suggestion that there has been virtually no passing of the drug into the systemic circulation.

After intracerebral implantation of PLAGA-5-FU microspheres in rodents, at a total dose of 17 mg/kg of 5-FU, no sign of systemic toxicity, nor any sign of clinical or histological neurotoxicity, was observed. At the fractionated dose of 24 Gy, the combination of 5-FU microspheres/cerebral radiotherapy is completely tolerated (Menei P, Vectorisation dans le SNC par implantation stéréotaxique de microspheres [Vectorization in the CNS by stereotactic implantation of microspheres], Theses d'Université en Sciences Pharmaceutiques [University doctorate in pharmaceutical sciences], Université d'Angers [University of Angers], 1995). Finally, these microspheres implanted by stereotaxy into a malignant glioma developed in rats (C6 glioma) significantly decrease mortality (Menei P, Boisdron-Celle M, Croue A, Guy G, Benoit J P, Effect of stereotactic implantation of biodegradable 5-fluorouracil-loaded microspheres in normal and C6-glioma bearing rats, Neurosurgery, 39: 117–124, 1996).

Advantageously, the microspheres are suspended in a sterile solution, the suspension being injected into the walls of the operating locus, after exeresis of the tumor.

The sterile solution preferably contains between 1 and 1.5%, preferably 1.25% weight/volume, of a viscosity modifier, for example sodium carboxymethylcellulose, between 0.5 and 1.5%, preferably 1%, of a surfactant, for example polysorbate 80®, and between 3.5 and 4.5%, preferably 4%, of an isotonicity agent, for example mannitol.

The microspheres are preferably suspended extemporaneously just before injection. The suspension preferably contains 3 ml of the sterile solution described above and 700 to 800 mg of biodegradable microspheres.

After confirmation of the diagnosis of glioblastoma and macroscopic exeresis of the glial tumor, the suspension of microspheres is implanted into the walls of the operating locus, at a depth of at least two centimeters, preferably between 2 and 3 centimeters, at least every $cm^2$.

When the anticancer agent is 5-FU, the total dose of suspension injected corresponds to an amount of 5-FU of between 50 and 200 mg.

The radiotherapy is focussed on the tumor volume, the volume irradiated encompasses the preoperative tumor with a margin of at least two centimeters in all directions, and a total dose of between 50 Gy and 60 Gy is applied.

The radiotherapy is preferably initiated between the second and seventh days after the operation. A total dose of between 50 Gy and 60 Gy is spread out over a period of time of between 4 and 8 weeks, for example at a rate of 5 fractions per week.

The radiotherapy is preferably carried out with a total dose of 60 Gy for approximately six weeks, preferably again at a rate of five fractions per week for 6.5 weeks.

After having injected the microspheres just after exeresis of the tumor, one or more new injections of microspheres may be performed by stereotaxy in the event of recurrence of the tumor.

The microspheres used in the context of the invention may be prepared using an emulsification-extraction technique according to a variation of the method described by Boisdron-Celle M, Menei P, Benoit J P: Preparation of biodegradable 5-fluorouracil-loaded microspheres, J Pharm Pharmacol, 47, 108–114, 1995.

The present invention also relates to a method for preparing the microspheres containing an anticancer agent, coated with a polymer used in the context of the invention. The major steps of this method consist in preparing an organic phase in which the anticancer agent and the polymer are dispersed in an organic solvent. The organic phase and an aqueous phase are emulsified, and then the organic solvent is extracted by adding water. Finally, the suspension of microspheres obtained is filtered.

The method of the invention is first of all characterized in that the anticancer agent is dispersed in the organic solvent, with vigorous stirring, before the polymer is added.

Depending on the adaptations made to the method of the prior art, the active principle is ground in a planetary ball mill. The size of the crystals obtained is between 15 and 50 $\mu$m. The size of the crystals to be encapsulated and their dispersion are, in fact, essential criteria for controlling the degree of encapsulation and the in vitro release kinetics.

The active principle is then dispersed in an organic solvent, preferably dichloromethane, in a round-bottomed tube, with stirring using a homogenization rod, before the polymer is added.

The homogenization gives a homogeneous suspension, attenuates the differences from one grinding batch to another and reduces the size of the crystals of the active principle.

The organic phase is prepared in a solvent without cosolvent. The absence of cosolvent slows down the precipitation of the polymer during the emulsification phase, such that the particles obtained are less porous.

The active principle dispersion is transferred into a first reactor.

The polymer is added in a proportion by mass of between 8 and 13%, preferably equal to 11%. The organic phase obtained is maintained at room temperature with constant stirring for 2 to 4 hours and then for approximately 15 minutes at a temperature of between 1 and 5° C., preferably equal to 2° C. A longer period of stirring of the organic phase at room temperature ensures total solubilization of the polymer in the solvent.

The aqueous phase is prepared in a second reactor, preferably maintaining it at the same temperature as the organic phase, preferably at 2° C. Reduction of the temperature of the aqueous phase and of the organic phase causes an increase in their viscosity and an increase in the degree of encapsulation. The aqueous phase is, for example, an aqueous 10% PVA solution.

Two jacketed reactors are used and a coolant liquid circulates in series in the two reactors. The temperature of the organic and aqueous phases is advantageously identical, preferably equal to 2° C., when the two phases are mixed together. Good control of the temperature effectively conditions the particle size, the rate of dissolution of the active principle and the extraction speed of the solvent all at once.

The organic phase is transferred from the first reactor into the second. The aqueous phase/organic phase proportion by volume is between 80/3 and 120/3, preferably equal to 100/3.

The emulsion obtained is stirred for at least 3 minutes, preferably for 3 to 6 minutes, even more preferably for 5 minutes. The choice of this period of time is directly correlated with the release kinetics and in particular the "burst" effect over 24–48 hours.

The absence of cosolvent coupled with a sufficient emulsification time allows dissolution of the active principle which is at the surface or poorly coated, such that the release kinetics in the initial phase are better controlled.

Water is added to the emulsion, in an emulsion/water ratio by volume of between 1/4 and 1/2, preferably equal to 1/3, in order to extract the organic solvent. The temperature of the extraction water is between 1 and 5° C., preferably equal to 4° C.

The emulsification and extraction steps are carried out in the same reactor so as to limit the variability from one batch to another and to save time. The temperature of the extraction water is low, so as to limit an excessive dissolution of the active principle.

The suspension of microspheres obtained is mixed for a few minutes and then filtered under an inert atmosphere. Working under an inert atmosphere makes it possible to limit the risks of contamination of the product.

The microspheres, which may be obtained according to the method described above, are advantageously lyophilized.

10 ml of sterile water are added to 2 to 5 g of microsphere powder (filtercake). This mixture is frozen at −40° C. and then introduced into the freeze-dryer. The lyophilization lasts 18 hours. At the end of the operation, the secondary drying temperature should be maintained below 10° C.

The microspheres should be stored at +40° C., even when dry.

The present invention also relates to a suspension consisting of a sterile solution containing 1 to 1.5% mass/volume of a viscosity modifier, 0.5 to 1.5% of a surfactant and 3.5 to 4.5% of an isotonicity agent, and biodegradable microspheres which release an anticancer agent, which are coated with a polymer and which are described above, optionally obtained according to the method described above, the proportion of the microspheres representing 200 to 300 mg/ml of sterile solution, preferably 230 to 270 mg/ml.

These microspheres preferably consist of 15 to 35% by weight of anticancer agent and 65 to 85% by weight of polymer.

The polymer is advantageously poly(d,1-lactic acid-co-glycolic acid) preferably containing an equal amount of lactic acid and glycolic acid.

The sterile solution preferably contains 1.25% weight/volume of sodium carboxymethylcellulose, 1% of polysorbate 80 and 4% of mannitol.

The present invention is illustrated in a nonlimiting manner by the following examples.

EXAMPLE 1

Microspheres prepared using the emulsification-extraction of solvent technique, according to a variation of the method described by Boisdron-Celle M, Menei P and Benoit J P (Preparation of biodegradable 5-fluorouracil-loaded microspheres, J Pharm Pharmacol, 47, 108–114, 1995).

Grinding of 5-FU

5-FU is ground in a planetary ball mill such as the Pulvérisette 7 (Fritsch). 8.5 g of 5-FU are introduced into a beaker containing 7 beads. The grinding lasts 10 minutes at speed 7. The powder is recovered under a laminar flow hood. The crystals obtained are between 15 and 50 $\mu$m in size and are divided into two fractions: a fine fraction (with a particle size of less than 1 $\mu$m) and a coarse fraction (greater than 30 $\mu$m).

Dispersion of 5-FU in the Organic Solvent

The ground 5-FU is dispersed in 45 ml of dichloromethane with stirring using a homogenizer such as an Ultra-Turrax machine for 3 minutes at 13 500 rpm, in a round-bottomed tube.

Preparation of the Organic Phase

The 5-FU dispersion is transferred into a 150 ml jacketed cooled reactor. The PLAGA is added thereto such that the PLAGA/dichloromethane proportion is equal to 11%. The organic phase is stirred with a paddle, at 450 rpm, for 4 hours at 20° C., and then for 15 minutes at 2° C. The temperature in the reactor is kept constant to within 0.1° C. with the aid of a cryostat.

Preparation of the Emulsion 1 500 ml of an autoclaved aqueous 10% PVA solution are prepared and maintained at 2° C. in a 6 liter jacketed cooled reactor. The organic phase is then transferred into this reactor by opening a base valve on the first reactor. The organic phase is poured over 5 to 10 s onto the aqueous phase, which is stirred using a paddle rotating at 375 rpm. The aqueous phase/organic phase proportion by volume is equal to 100/3.

The emulsion is stirred for 4 minutes and 45 s.

Extraction

When the emulsion is ready, 4.5 l of extraction water at 4° C. are poured onto the emulsion in an emulsion/water ratio by volume equal to 1/3. The extraction lasts 2 minutes.

Filtration

The entire contents of the second reactor are transferred, via the base, into a stainless steel tank and then placed under a pressure of nitrogen. The suspension is filtered through a filter with a pore diameter equal to 3 $\mu$m.

After passing the entire suspension through the filter, the filtercake is washed twice with 3 liters of sterile water.

The degree of encapsulation of the anticancer agent in the microspheres obtained is 20%. After sieving, desorption of the dichloromethane is performed in an oven for 48 hours. The microspheres are then packaged and sterilized by γ-irradiation at 19 kGy. Further monitoring of the degree of encapsulation is carried out after sterilization. An assay of the residual traces of solvent is then carried out. A residual level of dichloromethane of 0.5% is advantageously detected. The sterility and in vitro release kinetics of the microspheres obtained are monitored.

The microspheres obtained have an active principle content of 23±3.5%.

Several batches are produced according to the protocol described above and a mean particle size of 48±20 $\mu$m is calculated over the population of all of the batches, equivalent to 46±7$\mu$m (mean of the means of the batches prepared).

The microspheres obtained have an active principle content of 23±3.5% and a mean size of 48±20$\mu$m.

EXAMPLE 2

Microspheres are prepared using the emulsification-extraction of solvent technique of example 1.

Grinding of 5-FU

The procedure as in example 1 is carried out and 4 g of 5-FU are ground.

The crystals obtained are between 15 and 50 $\mu$m in size and are divided into two fractions: a fine fraction (with a particle size of less than 1 $\mu$m) and a coarse fraction (greater than 30 $\mu$m).

Dispersion of the 5-FU in the Organic Solvent

The ground 5-FU is dispersed in 40 ml of dichloromethane with stirring using a homogenizer such as an Ultra-Turrax machine for 3.5 minutes at 13 500 rpm, in a round-bottomed tube.

The organic phase and the emulsion are prepared as in example 1.

The extraction and filtration are carried out as in example 1.

Characteristics of the microspheres obtained.

5-FU content: 22%

Size: 46±7 $\mu$m

Burst effect at 24 h after radiosterilization at 19 kGy: 40±4%.

EXAMPLE 3

A phase I/II open pilot clinical study is carried out with the 50:50 PLAGA/5-FU microspheres of example 1.

The microspheres obtained are suspended extemporaneously in a solution containing 1.25% weight/volume of sodium carboxymethyl-cellulose (Cooper), 1% of polysorbate 80, 4% of mannitol, and a sufficient amount of water for injectable preparation, to obtain a total volume of 3 ml.

The solution is presterilized by autoclaving at 121° C. for 20 minutes, and then by radiosterilization by gamma-irradiation at a dose of between 5 kGy and 25 kGy, preferably 19 kGy.

The preparation of this suspension is delicate since the formation of bubbles has to be avoided. The suspension is injected immediately after it has been prepared, since the microspheres have a tendency to sediment in the syringe and block it.

The microsphere suspension is implanted into the walls of the operating locus, after macroscopic exeresis of the glial tumor, to a depth of between two and three centimeters, every cm$^2$, at a rate of 100 $\mu$l per injection.

The injection is performed with a 1 ml syringe and a catheter (Insyte® Vialon™) of 18 ga (1.3×45 mm), the metal mandrel of which is removed so as to retain only the unbeveled foam-tipped plastic catheter to inject the suspension into the cerebral tissue. As many 1 ml syringes as necessary are used. Injection of the suspension with the beveled needle introduces the risk of hematoma and backflow of the microspheres. The catheter should be small enough in diameter so as not to traumatize the cerebral tissue and large enough so as not to be blocked by the microsphere suspension.

The injection should be performed very gently and the catheter should remain in place for a few minutes before being removed, so as to avoid backflow of the microspheres. A 1 cm$^2$ fragment of resorbable hemostatic compress (Surgical® or Spongel®) is applied to the injection site.

The patients included in the study are between 18 and 68 years old, have no neoplastic history, have a Karnofsky index of greater than 60, have a clinical history and imaging evoking a sustentacular glioblastoma, have undergone a macroscopically complete exeresis, and their intraoperative histological examination (performed according to WHO criteria: necrosis, vascular proliferation, nuclear pleomorphism and mitotic activity) confirms the diagnosis of glioblastoma.

The criteria for excluding patients are as follows: metabolic deficiency, pregnancy, other prior cancer pathology.

Three groups were initially envisioned to study the effects of increasing doses of 5-fluorouracil: in chronological order, 70, 132 and 264 mg, the treatment of the following group being started after tolerance of the treatment by the group undergoing testing has been observed.

Due to the occurrence of Grade II neurological toxicity in a patient who received 132 mg of 5-FU, and according to the rules for stopping the protocol, the therapeutic escalation was stopped and the subsequent patients received the same dose of 132 mg.

Conventional external radiotherapy (focused on the tumor volume assessed on preoperative MRI with an energy of 10 MV) is initiated between the second and seventh days after the operation. A total dose of 60 Gy in 33 fractions of 1.8 Gy, at a rate of 5 fractions over 6.5 weeks, is applied. The volume irradiated encompasses the preoperative tumor with a margin of at least two centimeters in all directions.

The patients are monitored clinically and radiologically: a scan at 72 hours to confirm the macroscopically complete exeresis and a clinical assessment are carried out on D10, D20 and D30. MRI is carried out on D10 and D30. Finally, an assay of the 5-FU in the blood and the CSF is performed at 72 hours and on D10, D20 and D30. The toxicity (neurological, hematological, mucous membrane and cardiological) is assessed in grades on criteria derived from those of the WHO. After one month has passed, the patients are monitored clinically every two months and undergo MRI every three months.

Mild postoperative anemia, hyperleukocytosis and mild lymphopenia were observed in all the patients.

The pharmacological study confirmed the sustained release of 5-FU in the cerebrospinal fluid (CSF) for more than 30 days, and a transient passage, at a lower level, of the molecule into the systemic circulation. Significant concentrations of 5-FU are still present in the CSF one month after implantation.

The profiles of release of 5-FU in the CSF show a peak on the tenth and on the twentieth day, respectively, for doses of 70 and 132 mg. The level of 5-FU in the plasma was not detectable from the tenth day in half the patients.

The systemic tolerance is excellent in all the patients treated. No change in the chemistry or cellularity of the CSF was observed. The appearance of a cerebral edema during radiotherapy in a patient treated with 132 mg did not permit escalation of the dose to be continued.

Eight patients, including four males and four females, with an average age of 48.5 and a Karnofsky index of greater than 90, were thus included in the study. The first group of three received a dose of 70 mg, and the second group of five received 132 mg.

The preliminary results regarding survival could not be interpreted statistically due to the small number of patients. They were, however, very encouraging. At the final assessment, in the first group treated (70 mg), the three patients died at 61, 114 and 125 weeks. It should be noted that the patient who died at 114 weeks died of pulmonary metastases of the glioblastoma. In the second group treated (132 mg), three patients died at 31, 59 and 82 weeks and two were still in remission at 159 and 172 weeks, at the date of drafting of these preliminary results.

The survival median for the patients is 98 weeks (it is 50.6 weeks in the literature for patients satisfying the same criteria (Devaux B C, O'Fallon J R, Kelly P J, Resection, biopsy and survival in malignant glial neoplasms, J Neurosurg, 78: 767–775, 1993). Five out of eight patients, i.e. 62%, were alive at 18 months, whereas, in the literature, for patients satisfying the inclusion criteria of this study, the survival at 18 months is 20% (Devaux B C, O'Fallon J R, Kelly P J, Resection, biopsy and survival in malignant glial neoplasms, J Neurosurg, 78: 767–775, 1993).

What is claimed is:

1. A method for treating glioblastoma, comprising administrating biodegradable microspheres which contain and release 5-fluorouracile (5-FU), the microspheres being administrated simultaneously, separately, or spread out over time with radiotherapy and being intended to be implanted into an operating locus after excision of a glial tumor, wherein the microspheres containing the 5-FU are coated with a polymer which delays the release of the 5-FU and maintains, over time, a therapeutically effective concentration in the parenchymal space with a view to achieving a survival time for a patient thus treated of at least equal to approximately 90 weeks, wherein said microspheres comprise a neuroprotective compound chosen from peptide growth factors that are added to the 5-FU, and wherein said peptide growth factors are chosen from NGF and BDNF.

2. The method of claim 1, wherein said survival time for a patient thus treated is at least equal to approximately 130 weeks.

3. The method of claim 1, wherein said survival time for a patient thus treated is at least equal to approximately 160 weeks.

4. The method of claim 1, wherein the concentration of 5-FU in the cerebrospinal fluid, which mirrors the concentration in the parenchymal space, is from 3 to 20 ng/ml.

5. The method of claim 1, wherein said polymer coating which delays the release of the 5-FU maintains in the parenchymal space said therapeutically effective concentration in the parenchymal space for a period of at least 3 weeks.

6. The method of claim 5, wherein the period is at least 4 weeks.

7. The method of claim 1, wherein said polymer is chosen from ethylcellulose, polystyrene, poly($\epsilon$-caprolactone), poly(d, 1-lactic acid), and poly(d, 1-lactic acid-co-glycolic acid).

8. The method of claim 7, wherein said polymer is poly(d, 1-lactic acid-co-glycolic acid).

9. The method of claim 7, wherein said polymer is poly(d, 1-lactic acid-co-glycolic acid) containing an equal amount of lactic acid and of glycolic acid.

10. The method of claim 1, wherein said microspheres have a mean diameter of 48±20 $\mu$m.

11. The method of claim 10, wherein said mean diameter is 46±7 μm.

12. The method of claim 1, wherein said microspheres comprise from 15 to 35% by weight of 5-FU and from 65 to 85% by weight of said polymer.

13. The method of claim 12, wherein said microspheres comprise from 19 to 27% of 5-FU.

14. The method of claim 13, wherein said microspheres comprise about 20% of 5-FU.

15. The method of claim 1, wherein said microspheres are suspended in a sterile solution, wherein said suspension is intended to be injected into the walls of the operating locus after excision of the glial tumor.

16. The method of claim 15, herein said sterile solution comprises from 1 to 1.5% mass/volume of a viscosity modifier, from 0.5 to 1.5% of a surfactant, and from 3.5 to 4.5% of an isotonicity agent.

17. The method of claim 15, wherein said sterile solution has a microsphere concentration from 200 to 300 mg/ml.

18. The method of claim 16, wherein said solution comprises about 1.25% weight/volume of sodium carboxymethylcellulose, about 1% of polysorbate 80, and about 4% of mannitol.

19. The method of claim 15, wherein said suspension of microspheres is injected into the walls of said operating locus to a depth of at least 2 cm at least every $cm^2$.

20. The method of claim 19, wherein said depth is from 2 to 3 cm.

21. The method of claim 15, wherein the total dose of 5-FU injected is from 50 to 200 mg.

22. The method of claim 21, wherein said total dose of 5-FU injected is about 130 mg.

23. The method of claim 1, wherein said radiotherapy is focused on a tumor volume, wherein said volume irradiated encompasses a preoperative tumor with a margin of at least two centimeters in all directions, and wherein a total dose of from 50 to 60 Gy is applied.

24. The method of claim 1, wherein said radiotherapy is initiated during a day ranging from the second to seventh day post operation.

25. The method of claim 1, wherein said radiotherapy is performed with a total dose of about 60 Gy for a period of about six weeks.

26. The method of claim 15, wherein said suspension is injected by stereotaxy on one or more occasions in the event of recurrence of a tumor.

\* \* \* \* \*